United States Patent
Zubok et al.

(10) Patent No.: US 10,369,005 B2
(45) Date of Patent: *Aug. 6, 2019

(54) CERVICAL DISC REPLACEMENT

(71) Applicant: SpineCore, Inc., Allendale, NJ (US)

(72) Inventors: Rafail Zubok, Midland Park, NJ (US); Antonio Valdevit, Fishkill, NY (US); Michael W. Dudasik, Nutley, NJ (US); Joseph P. Errico, Warren, NJ (US)

(73) Assignee: SpineCore, Inc., Allendale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/992,705

(22) Filed: Jan. 11, 2016

(65) Prior Publication Data
US 2016/0120658 A1 May 5, 2016

Related U.S. Application Data

(63) Continuation of application No. 11/124,777, filed on May 9, 2005, now abandoned, which is a continuation
(Continued)

(51) Int. Cl.
*A61F 2/44* (2006.01)
*A61B 17/70* (2006.01)
(Continued)

(52) U.S. Cl.
CPC ........ *A61F 2/4425* (2013.01); *A61B 17/7059* (2013.01); *A61B 17/8033* (2013.01);
(Continued)

(58) Field of Classification Search
CPC .......................... A61F 2/4425; A61F 2002/443
See application file for complete search history.

(56) References Cited

U.S. PATENT DOCUMENTS 3,278,107 A 10/1966 Rygg
3,486,505 A 12/1969 Morrison
(Continued)

FOREIGN PATENT DOCUMENTS

EP 1224916 A2 7/2002
EP 1557143 A1 7/2005
(Continued)

OTHER PUBLICATIONS

MEDTRONIC: "Cornerstone-SR Cervical Carbon Cage System", Announcement Medtronic, Jan. 1, 1998, pp. 1-11, XP007916830.

*Primary Examiner* — Bruce E Snow
(74) *Attorney, Agent, or Firm* — Lerner, David, Littenberg, Krumholz & Mentlik, LLP

(57) ABSTRACT

A method for replacing at least a portion of an intervertebral disc in a spinal column includes: removing the portion of the intervertebral disc from the spinal column; and inserting an apparatus for replacing the portion of the intervertebral disc into an intervertebral disc space defined substantially between adjacent vertebral bones of the spinal column, and positioning the apparatus between the vertebral bones, wherein the apparatus is operable to permit the adjacent vertebral bones to articulate relative to one another about at least one of: (i) a first center of rotation for at least one of flexion and extension that is located outside the intervertebral disc space, and (ii) a second center of rotation for lateral bending that is located outside the intervertebral disc space.

5 Claims, 3 Drawing Sheets

Related U.S. Application Data of application No. 10/382,702, filed on Mar. 6, 2003, now Pat. No. 6,908,484.

(51) Int. Cl.

| | | |
|---|---|---|
| *A61B 17/80* | (2006.01) | |
| *A61B 17/86* | (2006.01) | |
| *A61F 2/46* | (2006.01) | |
| *A61F 2/30* | (2006.01) | |
| *A61B 17/17* | (2006.01) | |

(52) U.S. Cl.
CPC ...... *A61B 17/8042* (2013.01); *A61B 17/8625* (2013.01); *A61F 2/442* (2013.01); *A61F 2/4611* (2013.01); *A61F 2/4684* (2013.01); *A61B 17/1728* (2013.01); *A61B 17/866* (2013.01); *A61F 2002/3065* (2013.01); *A61F 2002/30301* (2013.01); *A61F 2002/30578* (2013.01); *A61F 2002/30616* (2013.01); *A61F 2002/30841* (2013.01); *A61F 2002/30843* (2013.01); *A61F 2002/449* (2013.01); *A61F 2002/4625* (2013.01); *A61F 2002/4627* (2013.01); *A61F 2002/4628* (2013.01); *A61F 2002/4629* (2013.01); *A61F 2230/0065* (2013.01); *A61F 2230/0095* (2013.01); *Y10S 623/908* (2013.01); *Y10S 623/911* (2013.01)

(56) References Cited

U.S. PATENT DOCUMENTS

| | | | |
|---|---|---|---|
| 3,872,519 A | | 3/1975 | Giannestras et al. |
| 4,021,864 A | | 5/1977 | Waugh |
| 4,105,407 A | | 8/1978 | Sanderson |
| 4,457,484 A | | 7/1984 | Hameister |
| 4,528,980 A | | 7/1985 | Kenna |
| 4,759,766 A | | 7/1988 | Buettner-Janz et al. |
| 4,759,769 A | | 7/1988 | Hedman et al. |
| 4,874,314 A | | 10/1989 | Fleer et al. |
| 4,917,704 A | | 4/1990 | Frey et al. |
| 4,955,908 A | | 9/1990 | Frey et al. |
| 4,997,432 A | * | 3/1991 | Keller .................. A61B 17/025 600/219 |
| 5,002,576 A | | 3/1991 | Fuhrmann et al. |
| 5,030,219 A | | 7/1991 | Matsen, III et al. |
| 5,122,130 A | | 6/1992 | Keller |
| 5,236,460 A | | 8/1993 | Barber |
| 5,258,031 A | | 11/1993 | Salib et al. |
| 5,314,477 A | | 5/1994 | Marnay |
| 5,370,697 A | | 12/1994 | Baumgartner |
| 5,401,269 A | | 3/1995 | Buttner-Janz et al. |
| 5,405,400 A | | 4/1995 | Linscheid et al. |
| 5,425,773 A | | 6/1995 | Boyd et al. |
| 5,458,641 A | | 10/1995 | Ramirez Jimenez |
| 5,507,816 A | | 4/1996 | Bullivant |
| 5,514,180 A | | 5/1996 | Heggeness et al. |
| 5,522,900 A | | 6/1996 | Hollister |
| 5,534,029 A | | 7/1996 | Shima |
| 5,549,690 A | | 8/1996 | Hollister et al. |
| 5,556,431 A | | 9/1996 | Buttner-Janz |
| 5,556,432 A | | 9/1996 | Kubein-Meesenburg et al. |
| 5,562,738 A | | 10/1996 | Boyd et al. |
| 5,599,279 A | | 2/1997 | Slotman et al. |
| 5,653,762 A | | 8/1997 | Pisharodi |
| 5,674,296 A | | 10/1997 | Bryan et al. |
| 5,676,701 A | | 10/1997 | Yuan et al. |
| 5,683,464 A | | 11/1997 | Wagner et al. |
| 5,683,465 A | | 11/1997 | Shinn et al. |
| 5,720,751 A | | 2/1998 | Jackson |
| 5,733,290 A | | 3/1998 | McCue et al. |
| 5,755,796 A | | 5/1998 | Ibo et al. |
| 5,769,856 A | | 6/1998 | Dong et al. |
| 5,782,830 A | | 7/1998 | Farris |
| 5,782,832 A | | 7/1998 | Larsen et al. |
| 5,865,846 A | | 2/1999 | Bryan et al. |
| 5,888,223 A | | 3/1999 | Bray, Jr. |
| 5,888,226 A | | 3/1999 | Rogozinski |
| 5,895,428 A | | 4/1999 | Berry |
| 5,899,941 A | | 5/1999 | Nishijima |
| 5,916,267 A | | 6/1999 | Tienboon |
| 5,928,284 A | | 7/1999 | Mehdizadeh |
| 5,989,291 A | | 11/1999 | Ralph et al. |
| 6,019,792 A | | 2/2000 | Cauthen |
| 6,039,763 A | | 3/2000 | Shelokov |
| 6,051,751 A | | 4/2000 | Sioshansi et al. |
| 6,063,121 A | | 5/2000 | Xavier et al. |
| 6,066,174 A | | 5/2000 | Farris |
| 6,066,175 A | | 5/2000 | Henderson et al. |
| 6,093,207 A | | 7/2000 | Pisharodi |
| 6,096,080 A | | 8/2000 | Nicholson et al. |
| 6,106,557 A | | 8/2000 | Robioneck et al. |
| 6,113,602 A | | 9/2000 | Sand |
| 6,113,637 A | * | 9/2000 | Gill .................. A61F 2/4425 623/17.15 |
| 6,113,638 A | | 9/2000 | Williams et al. |
| 6,139,550 A | | 10/2000 | Michelson |
| 6,143,012 A | | 11/2000 | Gausepohl |
| 6,146,421 A | | 11/2000 | Gordon et al. |
| 6,156,067 A | | 12/2000 | Bryan et al. |
| 6,159,215 A | | 12/2000 | Urbahns et al. |
| 6,174,311 B1 | | 1/2001 | Branch et al. |
| 6,179,873 B1 | | 1/2001 | Zientek |
| 6,179,874 B1 | | 1/2001 | Cauthen |
| 6,190,413 B1 | | 2/2001 | Sutcliffe |
| 6,193,757 B1 | | 2/2001 | Foley et al. |
| 6,213,055 B1 | | 4/2001 | Willinger et al. |
| 6,214,005 B1 | | 4/2001 | Benzel et al. |
| 6,217,615 B1 | | 4/2001 | Sioshansi et al. |
| 6,224,607 B1 | | 5/2001 | Michelson |
| 6,228,118 B1 | | 5/2001 | Gordon |
| 6,235,034 B1 | | 5/2001 | Bray |
| 6,235,060 B1 | | 5/2001 | Kubein-Meesenburg et al. |
| 6,241,769 B1 | | 6/2001 | Nicholson et al. |
| 6,277,149 B1 | | 8/2001 | Boyle et al. |
| 6,290,726 B1 | | 9/2001 | Pope et al. |
| 6,296,647 B1 | | 10/2001 | Robioneck et al. |
| 6,319,257 B1 | | 11/2001 | Carignan et al. |
| 6,325,828 B1 | | 12/2001 | Dennis et al. |
| 6,342,057 B1 | | 1/2002 | Brace et al. |
| 6,368,350 B1 | | 4/2002 | Erickson et al. |
| 6,395,030 B1 | | 5/2002 | Songer et al. |
| 6,395,032 B1 | | 5/2002 | Gauchet |
| 6,398,815 B1 | | 6/2002 | Pope et al. |
| 6,413,259 B1 | | 7/2002 | Lyons et al. |
| 6,416,551 B1 | | 7/2002 | Keller |
| 6,428,544 B1 | | 8/2002 | Ralph et al. |
| 6,432,106 B1 | | 8/2002 | Fraser |
| 6,436,102 B1 | | 8/2002 | Ralph et al. |
| 6,440,168 B1 | | 8/2002 | Cauthen |
| 6,461,359 B1 | | 10/2002 | Tribus et al. |
| 6,468,310 B1 | | 10/2002 | Ralph et al. |
| 6,471,725 B1 | | 10/2002 | Ralph et al. |
| 6,478,796 B2 | | 11/2002 | Zucherman et al. |
| 6,478,800 B1 | | 11/2002 | Fraser et al. |
| 6,517,580 B1 | | 2/2003 | Ramadan et al. |
| 6,524,312 B2 | | 2/2003 | Landry et al. |
| 6,527,320 B2 | | 3/2003 | Gregg |
| 6,527,804 B1 | | 3/2003 | Gauchet et al. |
| 6,540,785 B1 | | 4/2003 | Gill et al. |
| 6,562,073 B2 | | 5/2003 | Foley |
| 6,576,017 B2 | | 6/2003 | Foley et al. |
| 6,579,290 B1 | | 6/2003 | Hardcastle et al. |
| 6,579,320 B1 | | 6/2003 | Gauchet et al. |
| 6,579,321 B1 | | 6/2003 | Gordon et al. |
| 6,582,466 B1 | | 6/2003 | Gauchet |
| 6,582,468 B1 | | 6/2003 | Gauchet |
| 6,589,247 B2 | | 7/2003 | McGahan et al. |
| 6,602,292 B2 | | 8/2003 | Burkinshaw |
| 6,610,093 B1 | | 8/2003 | Pisharodi |
| 6,645,248 B2 | | 11/2003 | Casutt |
| 6,652,525 B1 | | 11/2003 | Assaker et al. |
| 6,652,533 B2 | | 11/2003 | O'Neil |
| 6,666,866 B2 | | 12/2003 | Martz et al. |

(56) References Cited

U.S. PATENT DOCUMENTS

| | | |
|---|---|---|
| 6,679,887 B2 | 1/2004 | Nicholson et al. |
| 6,679,915 B1 | 1/2004 | Cauthen |
| 6,682,562 B2 | 1/2004 | Viart et al. |
| 6,706,068 B2 | 3/2004 | Ferree |
| 6,716,245 B2 | 4/2004 | Pasquet et al. |
| 6,740,118 B2 | 5/2004 | Eisermann et al. |
| 6,743,257 B2 | 6/2004 | Castro |
| 6,793,678 B2 | 9/2004 | Hawkins |
| 6,800,093 B2 | 10/2004 | Nicholson et al. |
| 6,835,206 B2 | 12/2004 | Jackson |
| 6,837,905 B1 | 1/2005 | Lieberman |
| 6,896,676 B2 | 5/2005 | Zubok et al. |
| 6,908,484 B2 | 6/2005 | Zubok et al. |
| 6,936,071 B1 | 8/2005 | Marnay et al. |
| 6,972,037 B2 | 12/2005 | Zubok et al. |
| 6,972,038 B2 | 12/2005 | Zubok et al. |
| 6,981,990 B2 | 1/2006 | Keller |
| 6,986,789 B2 | 1/2006 | Schultz et al. |
| 6,991,654 B2 | 1/2006 | Foley |
| 6,994,727 B2 | 2/2006 | Khandkar et al. |
| 6,994,728 B2 | 2/2006 | Zubok et al. |
| 6,994,729 B2 | 2/2006 | Zubok et al. |
| 6,997,954 B2 * | 2/2006 | Zubok ............... A61B 17/7059 623/17.15 |
| 6,997,955 B2 | 2/2006 | Zubok et al. |
| 7,022,139 B2 | 4/2006 | Errico et al. |
| 7,056,344 B2 | 6/2006 | Huppert et al. |
| 7,063,725 B2 | 6/2006 | Foley |
| 7,125,425 B2 | 10/2006 | Foley et al. |
| 7,198,643 B2 | 4/2007 | Zubok et al. |
| 7,204,852 B2 | 4/2007 | Marnay et al. |
| 7,226,452 B2 | 6/2007 | Zubok et al. |
| 7,235,104 B2 | 6/2007 | Grinberg et al. |
| 7,270,679 B2 | 9/2007 | Istephanous et al. |
| 7,300,441 B2 | 11/2007 | Haid et al. |
| 7,320,689 B2 | 1/2008 | Keller |
| 7,537,614 B2 | 5/2009 | Baumgartner et al. |
| 7,637,911 B2 | 12/2009 | Zubok et al. |
| 7,794,465 B2 | 9/2010 | Marik et al. |
| 8,277,507 B2 | 10/2012 | Ferree et al. |
| 8,936,640 B2 * | 1/2015 | Zubok ............... A61B 17/8033 623/17.15 |
| 9,028,552 B2 * | 5/2015 | Zubok ............... A61B 17/8033 623/17.15 |
| 9,168,146 B2 | 10/2015 | Ferree et al. |
| 9,572,679 B2 | 2/2017 | Ferree et al. |
| 2001/0005796 A1 | 6/2001 | Zdeblick et al. |
| 2001/0007073 A1 | 7/2001 | Zucherman et al. |
| 2001/0010001 A1 | 7/2001 | Michelson |
| 2001/0012938 A1 | 8/2001 | Zucherman et al. |
| 2001/0020170 A1 | 9/2001 | Zucherman et al. |
| 2001/0027343 A1 | 10/2001 | Keller |
| 2002/0004683 A1 | 1/2002 | Michelson |
| 2002/0010511 A1 | 1/2002 | Michelson |
| 2002/0016595 A1 | 2/2002 | Michelson |
| 2002/0017789 A1 | 2/2002 | Holmes et al. |
| 2002/0035400 A1 | 3/2002 | Bryan et al. |
| 2002/0082597 A1 | 6/2002 | Fraser |
| 2002/0082701 A1 | 6/2002 | Zdeblick et al. |
| 2002/0099376 A1 | 7/2002 | Michelson |
| 2002/0107571 A1 | 8/2002 | Foley |
| 2002/0107572 A1 | 8/2002 | Foley et al. |
| 2002/0123750 A1 | 9/2002 | Eisermann et al. |
| 2002/0128712 A1 | 9/2002 | Michelson |
| 2002/0128715 A1 | 9/2002 | Bryan et al. |
| 2002/0128719 A1 | 9/2002 | Burkinshaw |
| 2002/0143399 A1 | 10/2002 | Sutcliffe |
| 2002/0147450 A1 | 10/2002 | LeHuec et al. |
| 2002/0165612 A1 | 11/2002 | Gerber et al. |
| 2002/0169508 A1 | 11/2002 | Songer et al. |
| 2002/0193880 A1 | 12/2002 | Fraser |
| 2003/0028197 A1 | 2/2003 | Hanson et al. |
| 2003/0028249 A1 | 2/2003 | Baccelli et al. |
| 2003/0040796 A1 | 2/2003 | Ferree |
| 2003/0040802 A1 | 2/2003 | Errico et al. |
| 2003/0045939 A1 | 3/2003 | Casutt |
| 2003/0060886 A1 | 3/2003 | Van Hoeck et al. |
| 2003/0069586 A1 | 4/2003 | Errico et al. |
| 2003/0074064 A1 | 4/2003 | Gerbec et al. |
| 2003/0078590 A1 | 4/2003 | Errico et al. |
| 2003/0078668 A1 | 4/2003 | Michelson |
| 2003/0093153 A1 | 5/2003 | Banick et al. |
| 2003/0100949 A1 | 5/2003 | Michelson |
| 2003/0109928 A1 | 6/2003 | Pasquet et al. |
| 2003/0114936 A1 | 6/2003 | Sherwood et al. |
| 2003/0120344 A1 | 6/2003 | Michelson |
| 2003/0125748 A1 | 7/2003 | Li et al. |
| 2003/0135278 A1 | 7/2003 | Eckman |
| 2003/0135279 A1 | 7/2003 | Michelson |
| 2003/0149482 A1 | 8/2003 | Michelson |
| 2003/0167091 A1 | 9/2003 | Scharf |
| 2003/0167092 A1 | 9/2003 | Foley |
| 2003/0176921 A1 | 9/2003 | Lawson |
| 2003/0176922 A1 | 9/2003 | Lawson et al. |
| 2003/0176923 A1 | 9/2003 | Keller et al. |
| 2003/0181982 A1 | 9/2003 | Kuslich |
| 2003/0187454 A1 | 10/2003 | Gill et al. |
| 2003/0191534 A1 | 10/2003 | Viart et al. |
| 2003/0195632 A1 | 10/2003 | Foley et al. |
| 2003/0199981 A1 | 10/2003 | Ferree |
| 2003/0199983 A1 | 10/2003 | Michelson |
| 2003/0204260 A1 | 10/2003 | Ferree |
| 2003/0208273 A1 | 11/2003 | Eisermann et al. |
| 2003/0216744 A1 | 11/2003 | Longhini et al. |
| 2003/0216810 A1 | 11/2003 | Ralph et al. |
| 2003/0229358 A1 | 12/2003 | Errico et al. |
| 2003/0229397 A1 | 12/2003 | Davis |
| 2003/0233097 A1 | 12/2003 | Ferree |
| 2003/0233146 A1 | 12/2003 | Grinberg et al. |
| 2003/0233148 A1 | 12/2003 | Ferree |
| 2004/0002759 A1 | 1/2004 | Ferree |
| 2004/0002762 A1 | 1/2004 | Hawkins |
| 2004/0006343 A1 | 1/2004 | Sevrain |
| 2004/0010254 A1 | 1/2004 | Cook et al. |
| 2004/0010316 A1 | 1/2004 | William et al. |
| 2004/0024459 A1 | 2/2004 | Ferree |
| 2004/0024461 A1 | 2/2004 | Ferree |
| 2004/0024462 A1 | 2/2004 | Ferree et al. |
| 2004/0030389 A1 | 2/2004 | Ferree |
| 2004/0030390 A1 | 2/2004 | Ferree |
| 2004/0030391 A1 | 2/2004 | Ferree |
| 2004/0034426 A1 | 2/2004 | Errico et al. |
| 2004/0039387 A1 | 2/2004 | Gause et al. |
| 2004/0068318 A1 | 4/2004 | Coates et al. |
| 2004/0068320 A1 | 4/2004 | Robie et al. |
| 2004/0073311 A1 | 4/2004 | Ferree |
| 2004/0117022 A1 | 6/2004 | Marnay et al. |
| 2004/0133281 A1 | 7/2004 | Khandkar et al. |
| 2004/0138750 A1 | 7/2004 | Mitchell |
| 2004/0143270 A1 | 7/2004 | Zucherman et al. |
| 2004/0143332 A1 | 7/2004 | Krueger et al. |
| 2004/0148028 A1 | 7/2004 | Ferree et al. |
| 2004/0167628 A1 | 8/2004 | Foley |
| 2004/0176772 A1 | 9/2004 | Zubok et al. |
| 2004/0176773 A1 | 9/2004 | Zubok et al. |
| 2004/0176774 A1 | 9/2004 | Zubok et al. |
| 2004/0176777 A1 | 9/2004 | Zubok et al. |
| 2004/0176778 A1 | 9/2004 | Zubok et al. |
| 2004/0176843 A1 | 9/2004 | Zubok et al. |
| 2004/0176852 A1 | 9/2004 | Zubok et al. |
| 2004/0193272 A1 | 9/2004 | Zubok et al. |
| 2004/0215198 A1 | 10/2004 | Marnay et al. |
| 2004/0220567 A1 | 11/2004 | Eisermann et al. |
| 2004/0243240 A1 | 12/2004 | Beaurain et al. |
| 2004/0267369 A1 | 12/2004 | Lyons et al. |
| 2005/0021042 A1 | 1/2005 | Marnay et al. |
| 2005/0033426 A1 | 2/2005 | Ogilvie et al. |
| 2005/0033430 A1 | 2/2005 | Powers et al. |
| 2005/0043800 A1 | 2/2005 | Paul et al. |
| 2005/0043803 A1 | 2/2005 | Schultz et al. |
| 2005/0055029 A1 | 3/2005 | Marik et al. |
| 2005/0071013 A1 | 3/2005 | Zubok et al. |
| 2005/0085917 A1 | 4/2005 | Marnay et al. |
| 2005/0143749 A1 | 6/2005 | Zalenski et al. |

(56) References Cited

U.S. PATENT DOCUMENTS

| | | |
|---|---|---|
| 2005/0159819 A1 | 7/2005 | McCormack et al. |
| 2005/0165487 A1 | 7/2005 | Muhanna et al. |
| 2005/0197705 A1 | 9/2005 | Amin et al. |
| 2005/0228497 A1 | 10/2005 | Ferree et al. |
| 2005/0228500 A1 | 10/2005 | Kim et al. |
| 2005/0240270 A1 | 10/2005 | Zubok et al. |
| 2005/0240271 A1 | 10/2005 | Zubok et al. |
| 2005/0240272 A1 | 10/2005 | Zubok et al. |
| 2005/0240273 A1 | 10/2005 | Khandkar et al. |
| 2005/0256577 A1 | 11/2005 | Baumgartner et al. |
| 2005/0267581 A1 | 12/2005 | Marnay et al. |
| 2005/0267582 A1 | 12/2005 | Ferree et al. |
| 2005/0283237 A1 | 12/2005 | Zucherman et al. |
| 2006/0004377 A1 | 1/2006 | Keller |
| 2006/0030857 A1 | 2/2006 | de Villiers et al. |
| 2006/0036326 A1 | 2/2006 | Baumgartner et al. |
| 2006/0069439 A1 | 3/2006 | Zucherman et al. |
| 2006/0085077 A1 | 4/2006 | Cook et al. |
| 2006/0116768 A1 | 6/2006 | Krueger et al. |
| 2006/0149273 A1 | 7/2006 | Ross |
| 2006/0167461 A1 | 7/2006 | Hawkins et al. |
| 2006/0178748 A1 | 8/2006 | Dinger et al. |
| 2006/0217731 A1 | 9/2006 | Gil et al. |
| 2006/0282020 A1 | 12/2006 | Bertagnoli et al. |
| 2007/0073403 A1 | 3/2007 | Lombardo et al. |
| 2007/0073405 A1 | 3/2007 | Verhulst et al. |
| 2007/0106388 A1 | 5/2007 | Michelson |
| 2007/0112429 A1 | 5/2007 | Muhanna et al. |
| 2007/0118224 A1 | 5/2007 | Shah et al. |
| 2007/0225813 A1 | 9/2007 | Haines |
| 2007/0265707 A1 | 11/2007 | Marnay et al. |
| 2007/0282448 A1 | 12/2007 | Abdou |
| 2008/0027548 A9 | 1/2008 | Ferree et al. |
| 2008/0033563 A1 | 2/2008 | Khandkar |
| 2008/0082169 A1 | 4/2008 | Gittings et al. |
| 2009/0018663 A1 | 1/2009 | Cook et al. |
| 2012/0016480 A1 | 1/2012 | Gerber et al. |

FOREIGN PATENT DOCUMENTS

| | | |
|---|---|---|
| FR | 2 718 635 A1 | 10/1995 |
| FR | 2730159 | 8/1996 |
| FR | 2805985 A1 | 9/2001 |
| FR | 2824261 | 11/2002 |
| JP | 06-007390 A | 1/1994 |
| JP | 07-241306 A | 9/1995 |
| JP | 08-080311 A | 3/1996 |
| JP | 2000-139971 A | 5/2000 |
| JP | 2000-152943 A | 6/2000 |
| JP | 2002-528171 A | 9/2002 |
| JP | 2006-519673 A | 8/2006 |
| WO | 91/13598 A1 | 9/1991 |
| WO | 94/04100 A1 | 3/1994 |
| WO | 9509587 A1 | 4/1995 |
| WO | 9710780 A1 | 3/1997 |
| WO | 9720526 A1 | 6/1997 |
| WO | 0024342 A1 | 5/2000 |
| WO | 00 66045 A1 | 11/2000 |
| WO | 0066011 A1 | 11/2000 |
| WO | 0101893 A1 | 1/2001 |
| WO | 0156497 A2 | 8/2001 |
| WO | 0156513 A1 | 8/2001 |
| WO | 0195838 A1 | 12/2001 |
| WO | 0207654 A2 | 1/2002 |
| WO | 02078514 A2 | 10/2002 |
| WO | 03053290 A1 | 7/2003 |
| WO | 03077808 A2 | 9/2003 |
| WO | 03/084449 A1 | 10/2003 |
| WO | 03090649 A1 | 11/2003 |
| WO | 2004/019828 A1 | 3/2004 |
| WO | 2004/026186 A1 | 4/2004 |

* cited by examiner

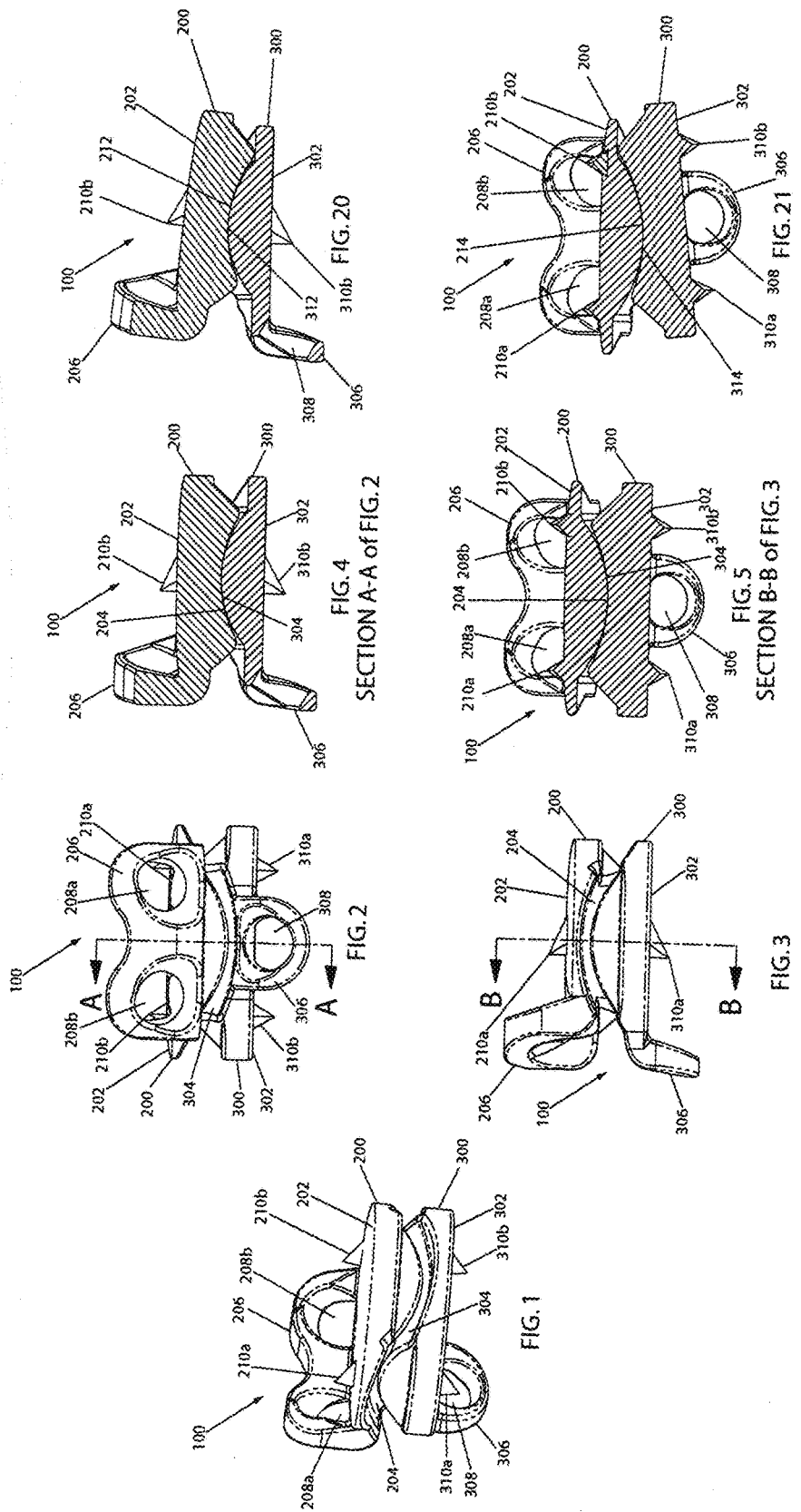

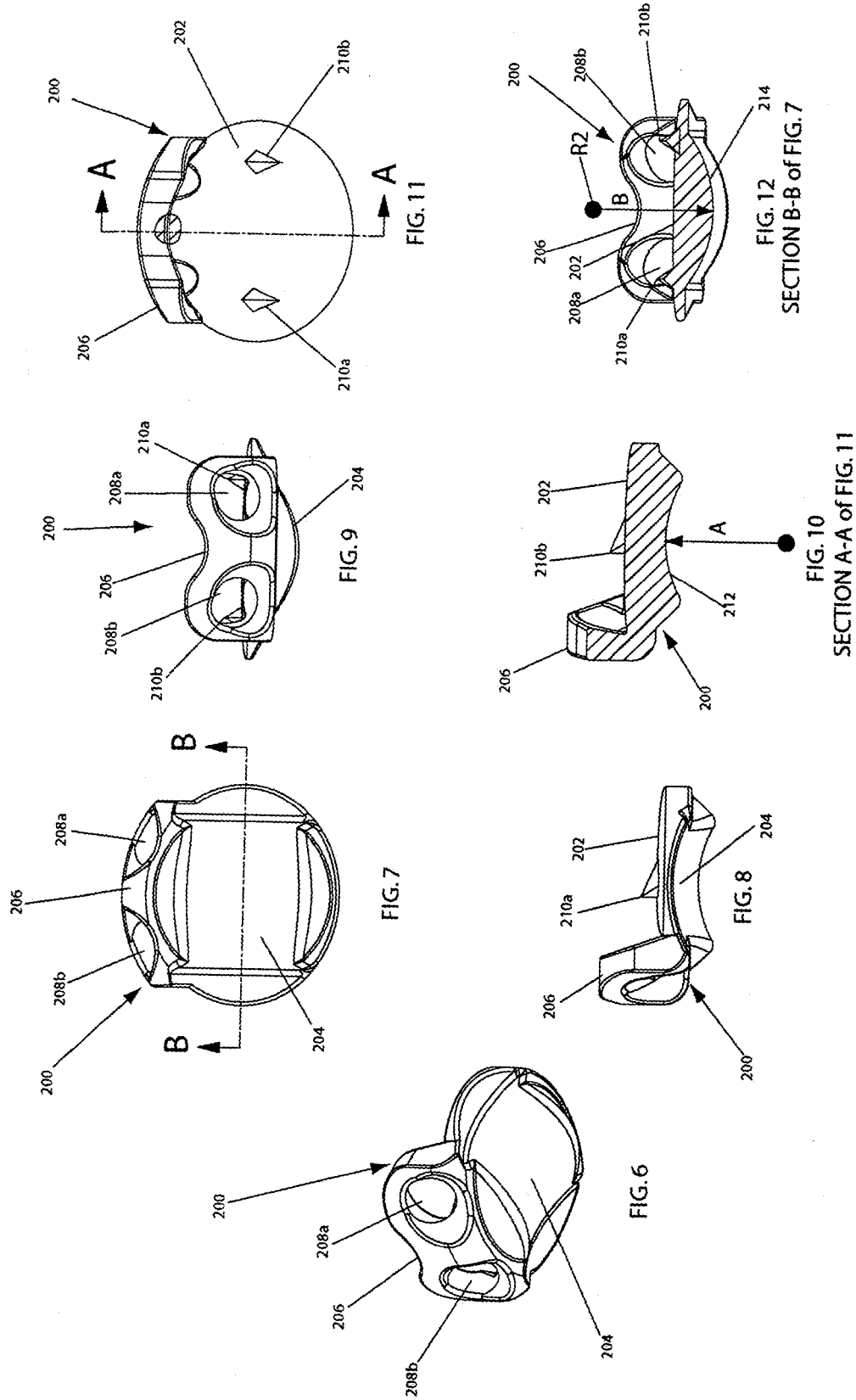

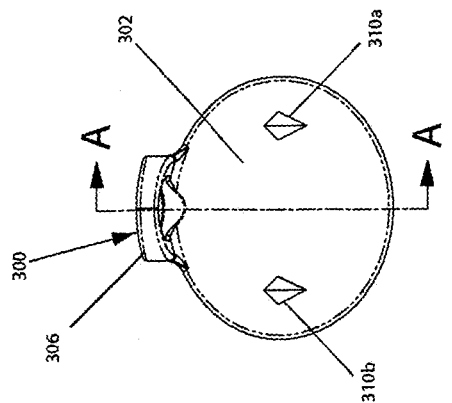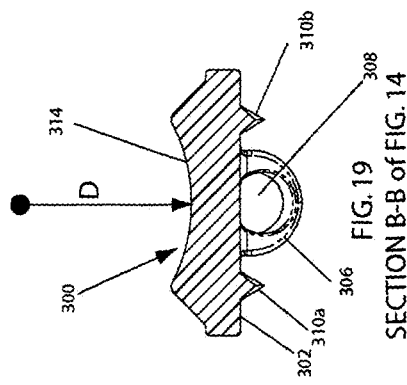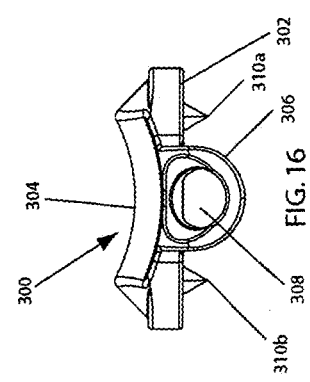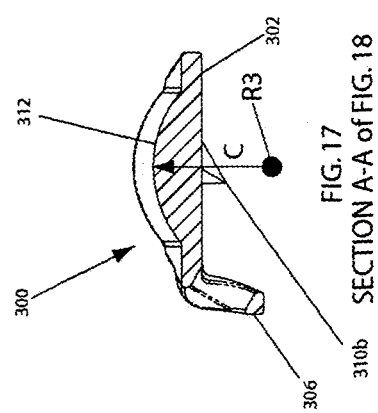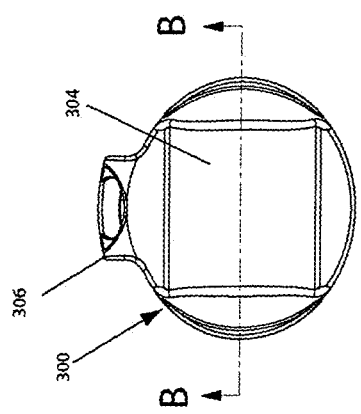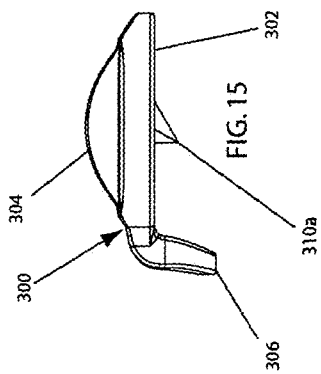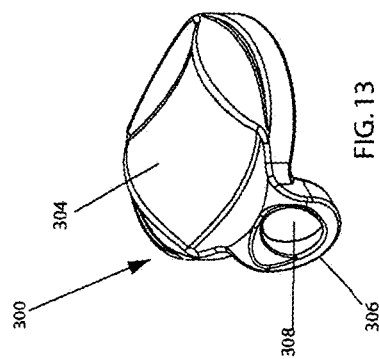

CERVICAL DISC REPLACEMENT

CROSS REFERENCE TO RELATED APPLICATIONS

This application is a continuation of U.S. patent application Ser. No. 11/124,777, filed May 9, 2005, which is a continuation of U.S. patent application Ser. No. 10/382,702, filed on Mar. 6, 2003, the disclosures of which are incorporated herein by reference.

BACKGROUND OF THE INVENTION

The present invention is directed to a cervical joint replacement implant and more particularly to a cervical intervertebral disc prosthesis having opposing constant radii saddle shaped articulating surfaces.

The structure of the intervertebral disc disposed between the cervical bones in the human spine comprises a peripheral fibrous shroud (the annulus) which circumscribes a spheroid of flexibly deformable material (the nucleus). The nucleus comprises a hydrophilic, elastomeric cartilaginous substance that cushions and supports the separation between the bones while also permitting articulation of the two vertebral bones relative to one another to the extent such articulation is allowed by the other soft tissue and bony structures surrounding the disc. The additional bony structures that define pathways of motion in various modes include the posterior joints (the facets) and the lateral intervertebral joints (the unco-vertebral joints). Soft tissue components, such as ligaments and tendons, constrain the overall segmental motion as well.

Traumatic, genetic, and long term wearing phenomena contribute to the degeneration of the nucleus in the human spine. This degeneration of this critical disc material, from the hydrated, elastomeric material that supports the separation and flexibility of the vertebral bones, to a flattened and inflexible state, has profound effects on the mobility (instability and limited ranges of appropriate motion) of the segment, and can cause significant pain to the individual suffering from the condition. Although the specific causes of pain in patients suffering from degenerative disc disease of the cervical spine have not been definitively established, it has been recognized that pain may be the result of neurological implications (nerve fibers being compressed) and/or the subsequent degeneration of the surrounding tissues (the arthritic degeneration of the facet joints) as a result of their being overloaded.

Traditionally, the treatment of choice for physicians caring for patients who suffer from significant degeneration of the cervical intervertebral disc is to remove some, or all, of the damaged disc. In instances in which a sufficient portion of the intervertebral disc material is removed, or in which much of the necessary spacing between the vertebrae has been lost (significant subsidence), restoration of the intervertebral separation is required.

Unfortunately, until the advent of spine arthroplasty devices, the only methods known to surgeons to maintain the necessary disc height necessitated the immobilization of the segment. Immobilization is generally achieved by attaching metal plates to the anterior or posterior elements of the cervical spine, and the insertion of some osteoconductive material (autograft, allograft, or other porous material) between the adjacent vertebrae of the segment. This immobilization and insertion of osteoconductive material has been utilized in pursuit of a fusion of the bones, which is a procedure carried out on tens of thousands of pain suffering patients per year.

This sacrifice of mobility at the immobilized, or fused, segment, however, is not without consequences. It was traditionally held that the patient's surrounding joint segments would accommodate any additional articulation demanded of them during normal motion by virtue of the fused segment's immobility. While this is true over the short-term (provided only one, or at most two, segments have been fused), the effects of this increased range of articulation demanded of these adjacent segments has recently become a concern. Specifically, an increase in the frequency of returning patients who suffer from degeneration at adjacent levels has been reported.

Whether this increase in adjacent level deterioration is truly associated with rigid fusion, or if it is simply a matter of the individual patient's predisposition to degeneration is unknown. Either way, however, it is clear that a progressive fusion of a long sequence of vertebrae is undesirable from the perspective of the patient's quality of life as well as from the perspective of pushing a patient to undergo multiple operative procedures.

While spine arthroplasty has been developing in theory over the past several decades, and has even seen a number of early attempts in the lumbar spine show promising results, it is only recently that arthoplasty of the spine has become a truly realizable promise. The field of spine arthroplasty has several classes of devices. The most popular among these are: (a) the nucleus replacements, which are characterized by a flexible container filled with an elastomeric material that can mimic the healthy nucleus; and (b) the total disc replacements, which are designed with rigid endplates which house a mechanical articulating structure that attempts to mimic and promote the healthy segmental motion.

Among these solutions, the total disc replacements have begun to be regarded as the most probable long-term treatments for patients having moderate to severe lumbar disc degeneration. In the cervical spine, it is likely that these mechanical solutions will also become the treatment of choice. At present, there are two devices being tested clinically in humans for the indication of cervical disc degeneration. The first of these is the Bryan disc, disclosed in part in U.S. Pat. No. 6,001,130. The Bryan disc is comprised of a resilient nucleus body disposed in between concaval-covex upper and lower elements that retain the nucleus between adjacent vertebral bodies in the spine. The concaval-convex elements are L-shaped supports that have anterior wings that accept bones screws for securing to the adjacent vertebral bodies.

The second of these devices being clinically tested is the Bristol disc, disclosed substantially in U.S. Pat. No. 6,113,637. The Bristol disc is comprised of two L-shaped elements, with corresponding ones of the legs of each element being interposed between the vertebrae and in opposition to one another. The other of the two legs are disposed outside of the intervertebral space and include screw holes through which the elements may be secured to the corresponding vertebra; the superior element being secured to the upper vertebral body and the inferior element being attached to the lower vertebral body. The opposing portions of each of the elements comprise the articulating surfaces that include an elliptical channel formed in the lower element and a convex hemispherical structure disposed in the channel.

As is evident from the above descriptions, the centers of rotation for both of these devices, which are being clinically tested in human subjects, is disposed at some point in the disc space. More particularly with respect to the Bryan disc, the center of rotation is maintained at a central portion of the nucleus, and hence in the center of the disc space. The Bristol disc, as a function of its elongated channel (its elongated axis being oriented along the anterior to posterior direction), has a moving center of rotation which is, at all times maintained within the disc space at the rotational center of the hemispherical ball (near the top of the upper element).

Other aspects, features and advantages of the present invention not already evident will become evident from the description herein taken in conjunction with the accompanying drawings.

SUMMARY OF THE INVENTION

The present invention provides an articulating joint implant that includes a pair of opposing upper and lower elements having nested articulation surfaces providing a center of rotation of the implant above the adjacent vertebral body endplate surfaces in one mode of motion (e.g., lateral bending) and a center of rotation of the implant below those surfaces in another mode of motion (e.g., flexion/extension), and that further permit axial rotation of the opposing elements relative to one another (for example, about an axis such as, for example, a longitudinal axis, for example, of the spinal column)) through a range of angles without causing them to move in directions that are directed away from one another (for example, in opposing directions along the axis of axial rotation) within that range. In preferred embodiments, the articulation surfaces further cause such opposite (or otherwise directed away from one another) movement of the opposing elements beyond that range.

More particularly, the present invention contemplates that with regard to the cervical anatomy, a device that maintains a center of rotation, moving or otherwise, within the disc space is inappropriate and fails to properly support healthy motion. Specifically, the cervical joint comprises five separate articulating elements: the facet joints in the posterior of the segment; the lateral unco-vertebral joints; and the nucleus in the intervertebral space. It is contemplated by the present invention that a track defined by the cervical facets falls along the planes between the inferior surface of the upper facets and the superior surface of the lower facets, and that this plane extends upwardly and forward, forcing the overall joint to pivot around a center of rotation that resides in the lower vertebral bone in flexion/extension articulation.

Conversely, it is contemplated by the present invention that in lateral bending the unco-vertebral joints influence the track of motion. Specifically, the unco-vertebral joints are formed at the lateral edges of the intervertebral space and are defined by a pair of upwardly extending surfaces of the inferior vertebral endplate and the corresponding surfaces of the superior bony endplate. It is contemplated by the present invention that this U-shaped configuration guides the segment into a rotation about a center within the superior vertebral bone during lateral bending.

Finally, it is contemplated by the present invention that during axial rotation of the adjacent vertebral bones of the cervical segment relative to one another about the longitudinal axis of the spinal column, the opposing bones do not simply axially rotate relative to one another for more than a few degrees, but rather follow the coupled influences of the unco-vertebral joints and the nucleus, and that this coupled motion vertically separates the opposing bones of the facet joints as the rotation continues, thus freeing the bones to rotate farther that would otherwise be permitted if the facets locked together (as is often seen as a symptom of degenerative cervical disease).

Both the Bryan and Bristol discs described above do provide distraction and maintenance of intervertebral disc height, and thereby provide immediate and short-term relief from pain. However, it should be understood, in light of the above described anatomy as contemplated by the present invention, that neither provides for proper anatomical motion because their respective centers of rotation are located within the disc space. Thus, neither will afford significant motion preservation, and patients with these devices implanted in their necks will find no significant mobility at the implanted segment. This may lead to spontaneous fusions, long term facet deterioration, and/or accelerated adjacent level degeneration.

The constraints placed on the prosthesis by the above-described anatomy are considerable. To provide an implant having a pair of articulation surfaces that provide a center of rotation of the implant above the surfaces in one mode of motion (lateral bending) and a center of rotation of the implant below the surfaces in another mode of motion (flexion/extension), that further permit the surfaces to axially rotate relative to one another about a longitudinal axis of the spinal column through a range of angles without causing movement of the surfaces in opposing directions along the longitudinal axis of the spinal column, and that further cause such movement (and accordingly a vertical separation of the facet joints) beyond that range is a difficult engineering task. The present invention contemplates that a saddle joint provides a geometric approach to the task.

The solution to this problem, however, is not open to just any saddle joint configuration. U.S. Pat. Nos. 5,405,400 and 5,645,605 describe saddle joints utilized for prosthetic thumb joints. More particularly, U.S. Pat. No. 5,405,400 ("Linscheid") discloses an artificial thumb joint comprising a pair of surfaces that are nesting hyperbolic paraboloids. A hyperbolic paraboloid is a surface defined by a first specific geometric form (the hyperbola) that is swept along a second geometric form (the parabola) that is perpendicular to the first form, and which first and second forms are opposite in the direction of their convexities. A common feature of both hyperbolae and parabolae is that neither has a constant radius of curvature along its extent. Constant radii of curvature are necessary for a pair of surfaces to smoothly flow over one another. Accordingly, the nesting hyperbolic paraboloids set forth in the reference are, therefore, not capable of any smooth articulation. Any attempted articulation causes the two surfaces to immediately move in opposing directions. Stated more simply, nesting hyperbolic paraboloids have continuously changing centers of rotation (by the nature of the geometric forms selected). The present invention contemplates that the cervical joint anatomy enables smooth articulation in two modes of motion (lateral bending and flexion/extension), and also smooth relative axial rotation about the longitudinal axis of the spinal column through a small range of angles. It is understood by the present invention that the vertical separation motion of the natural cervical joint does not occur immediately, but rather occurs only outside that small angular range of relative axial rotation. Thus, the present invention contemplates that the nesting hyperbolic paraboloids disclosed by Linscheid are inappropriate for use in the cervical joint.

U.S. Pat. No. 5,645,605 ("Klawitter") discloses an alternate form of a saddle surface, again for use in an artificial thumb joint that comprises a pair of nesting toroidal surfaces. Toroidal surfaces are defined by an arc of one circle being swept along an arc of another, again having opposing convexities. As circles have constant radii of curvatures, it is possible with these surfaces to have smooth motion in two perpendicular planes. More particularly, if the corresponding radii of curvature are approximately equivalent, the two surfaces may nest and articulate in flexion/extension and lateral bending smoothly, without causing the surfaces to move in opposing directions upon an attempted articulation. However, Klawitter teaches that these toroidal surfaces should have the same radii of curvature, inasmuch as it is a necessity that axial rotational motion of the joint be inhibited, or if it is permitted to occur, it should cause an immediate axial distraction of the joint. As explained above with regard to the saddle joint in Linscheid, this elimination of the capacity of the surfaces to axially rotate relative to one another for even a small range of angles prevents such a design from being effectively used in a cervical disc application.

In order for two nesting toroidal saddles to rotate within the same plane, each of the concave radii of the surfaces must be greater than the radius of its nested convex surface. An artificial cervical joint that provides a center of rotation in the vertebral bone below during flexion/extension and in the vertebral bone above during lateral bending and has the capacity to axially rotate within a small range of angles prior to causing oppositely directed movement of the surfaces requires nesting surfaces with such a configuration.

The present invention, therefore, provides an articulating joint implant for use in the cervical spine, including a first (e.g., upper) element and a second (e.g., lower) element, each having an outwardly facing vertebral body contact surface, and each having an inwardly facing articulation surface. The elements are disposed with the articulation surfaces nested against one another, and the vertebral body contact surfaces facing away from one another. When the implant is disposed in an intervertebral disc space in a cervical spine, in this configuration and with the vertebral body contact surfaces engaged with respective adjacent vertebral body endplates, the implant enables the adjacent vertebral bones to move relative to one another in accordance with proper anatomical motion.

Preferably, each of the elements has at least one long-term fixation structure (e.g., a flange) having at least one feature (e.g., a through hole) for securing the element to an adjacent vertebral body. For example, the upper element has an anterior flange that extends upwardly and has two through holes, each of which accepts a bone screw. And, for example, the lower element has an anterior flange that extends downwardly and has one through hole that accepts a bone screw. Further preferably, each of the elements has at least one short-term fixation structure (e.g., spikes on the outwardly directed vertebral body contact surface) for securing the element to an adjacent vertebral body endplate.

Further preferably, each of the outwardly directed vertebral body contact surfaces is shaped to conform to the endplate of an adjacent vertebral body against which it is to be positioned. For example, vertebral body contact surface of the upper element is curvate (to match the anatomy of the superior vertebral body endplate) and the vertebral body contact surface of the lower element is flat (to match the anatomy of the inferior vertebral body endplate). Further preferably, each vertebral body contact surface has an osteoinductive or osteoconductive feature, such as, for example, porous or rough areas.

The longitudinally inwardly directed articulation surface of the upper element forms a constant radii saddle-shaped articulation surface. More particularly, the saddle surface is defined by a concave arc that is swept perpendicular to and along a convex arc. The articulation surface has a cross-section in one plane that forms a concave arc, and a cross-section in another plane (perpendicular to that plane) that forms a convex arc. The concave arc has a respective constant radius of curvature about an axis perpendicular to the one plane. The convex arc has a respective constant radius of curvature about an axis perpendicular to the other plane.

In a preferred embodiment, the concave arc has a constant radius of curvature A about an axis perpendicular to the anterior-posterior plane, and the convex arc has a constant radius of curvature B about an axis perpendicular to the lateral plane. Preferably, radius A is less than radius B.

The longitudinally inwardly directed articulation surface of the lower element also forms a constant radii saddle-shaped articulation surface. More particularly, the saddle surface is defined by a convex arc that is swept perpendicular to and along a concave arc. The articulation surface has a cross-section in one plane that forms a convex arc, and a cross-section in another plane (perpendicular to that plane) that forms a concave arc. The convex arc has a respective constant radius of curvature about an axis perpendicular to the one plane. The concave arc has a respective constant radius of curvature about an axis perpendicular to the other plane.

In a preferred embodiment, the convex arc has a constant radius of curvature C about an axis perpendicular to the anterior-posterior plane, and the concave arc has a constant radius of curvature D about an axis perpendicular to the lateral plane. Preferably, radius C is less than radius D.

The constant radii saddle shaped articulation surfaces are configured and sized to be nestable against one another and articulatable against one another, to enable adjacent vertebral bones (against which the upper and lower elements are respectively disposed in the intervertebral space) to articulate in flexion, extension, and lateral bending. More particularly, the artificial disc implant of the present invention is assembled by disposing the upper and lower elements such that the vertebral body contact surfaces are directed away from one another, and the articulation surfaces are nested against one another such that the concave arcs accommodates the convex arcs.

Accordingly, movement of the adjacent vertebral bones relative to one another is permitted by the movement of the upper and lower elements relative to one another. In flexion and extension, the concave arcs of the upper element ride on the convex arcs of the lower element about a center of rotation below the articulation surfaces. In lateral bending, the concave arcs of the lower element ride on the convex arcs of the upper element about a center of rotation above the articulation surfaces. During these articulations, the elements are maintained at constant relative distraction positions, i.e., the elements do not move in directions that are directed away from one another (for example, do not move in opposing axial directions from one another (e.g., along a longitudinal axis of the spine)). Accordingly, the present invention provides a pair of articulation surfaces that have a center of rotation above the surfaces in one mode of motion (lateral bending), and below the surfaces in another (flexion/extension), consistent in these regards with a natural cervical intervertebral joint. Preferably, the articulation surfaces are sized and configured so that the respective ranges of angles through which flexion/extension and lateral bending can be experienced are equal to or greater than the respective normal physiologic ranges for such movements in the cervical spine.

It is preferable that, in addition to the flexion, extension, and lateral bending motions described above, the adjacent vertebral bones be permitted by the artificial disc implant to axially rotate relative to one another (e.g., about the longitudinal axis of the spinal column), through a small range of angles, without moving in opposite (or otherwise directed away from one another) directions (e.g., along the longitudinal axis) within that range, and then to engage in such opposite (or otherwise directed away from one another) movement once that range is exceeded. Preferably, the articulation surfaces 204, 304 are accordingly configured and sized to permit such movements. In a preferred configuration, the constant radius of curvature A is larger than the constant radius of curvature C, and the constant radius of curvature D is larger than the constant radius of curvature B. Because of the space, afforded by the differing radii, at the edges of the articulation surfaces, the upper and lower elements are able to axially rotate relative to one another about the longitudinal axis of the spinal column through a range of angles without causing the vertebral body contact surfaces to move away from one another along the longitudinal axis. Once the axial rotation exceeds that range, the articulation surfaces interfere with one another as the concave arcs move toward positions in which they would be parallel to one another, and the distance between the vertebral body contact surfaces increases with continued axial rotation as the concave arcs ride up against their oppositely directed slopes. Thus, the articulation surfaces are configurable according to the present invention to permit normal physiologic axial rotational motion of the adjacent vertebral bones about the longitudinal axis through a range of angles without abnormal immediate axially opposite (or otherwise directed away from one another) movement, and to permit such axially opposite (or otherwise directed away from one another) movement when under normal physiologic conditions it should occur, that is, outside that range of angles.

In preferred embodiments where the constant radius of curvature A is larger than the constant radius of curvature C, and the constant radius of curvature D is larger than the constant radius of curvature B, the articulation surfaces maintain point-to-point contact over a range of normal physiologic articulating movement between the adjacent vertebral bones. That is, through flexion, extension, lateral bending, and axial rotation, the articulation surfaces are in point-to-point contact with one another.

Preferably, the surface area dimensions of the articulation surfaces are selected in view of the selected radii of curvature to prevent the edges of the saddle surfaces (particularly the edges of the concave arcs) from hitting any surrounding anatomic structures, or other portions of the opposing upper or lower element, before the limit of the normal physiologic range of an attempted articulation is reached.

In accordance with one or more aspects of the present invention, an apparatus for replacing at least a portion of an intervertebral disc in a spinal column includes: a first member having a first vertebral contact surface for engagement with an endplate of a first vertebral bone in the spinal column, and having a first articulation surface; and a second member having a second vertebral contact surface for engagement with an endplate of a second vertebral bone in the spinal column, and having a second articulation surface, wherein: an intervertebral disc space is defined substantially between the first and second endplates of the first and second vertebral bones, and at least one of the first and second articulation surfaces is a saddle shaped surface, and the articulation surfaces are sized and shaped to engage one another when the first and second members are disposed in the intervertebral disc space to enable the first and second vertebral bones to articulate in at least one of flexion, extension, and lateral bending.

In accordance with one or more aspects of the present invention, a method for replacing at least a portion of an intervertebral disc in a spinal column includes: removing the portion of the intervertebral disc from the spinal column; and inserting an apparatus for replacing the portion of the intervertebral disc into an intervertebral disc space defined substantially between adjacent vertebral bones of the spinal column, and positioning the apparatus between the vertebral bones, wherein the apparatus is operable to permit the adjacent vertebral bones to articulate relative to one another about at least one of: (i) a first center of rotation for at least one of flexion and extension that is located outside the intervertebral disc space, and (ii) a second center of rotation for lateral bending that is located outside the intervertebral disc space.

The novel features of the present invention, as well as the invention itself, both as to its structure and its operation will be understood from the accompanying drawings, taken in conjunction with the accompanying description, in which similar reference characters refer to similar parts throughout.

BRIEF DESCRIPTION OF THE DRAWINGS

FIGS. 1-5 show an artificial disc implant of the present invention in perspective, anterior, lateral, lateral cutaway, and posterior cutaway views, respectively.

FIGS. 6-12 show an upper element of the artificial disc implant of FIGS. 1-5 in perspective, bottom (looking longitudinally up), lateral, anterior, lateral cutaway, top (looking longitudinally down), and posterior cutaway views, respectively.

FIGS. 13-19 show a lower element of the artificial disc implant of FIGS. 1-5 in perspective, top (looking longitudinally down), lateral, anterior, lateral cutaway, bottom (looking longitudinally up), and posterior cutaway views, respectively.

FIG. 20 shows a lateral cross-section view of the artificial disc implant of FIGS. 1-5 in extension.

FIG. 21 shows a posterior cross-section view of the artificial disc implant of FIGS. 1-5 in lateral bending.

DESCRIPTION OF THE PREFERRED EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Referring now to FIGS. 1-5, an artificial disc implant 100 of the present invention is shown in perspective, anterior, lateral, lateral cutaway, and posterior cutaway views, respectively. The implant 100 includes a first (e.g., upper) element 200 and a second (e.g., lower) element 300, each having an outwardly facing vertebral body contact surface 202, 302, and each having an inwardly facing articulation surface 204, 304. The elements 200, 300 are disposed as shown with the articulation surfaces 204, 304 nested against one another, and the vertebral body contact surfaces 202, 302 facing away from one another. When the implant 100 is disposed in an intervertebral disc space in a cervical spine, in this configuration and with the vertebral body contact surfaces 202, 302 engaged with respective adjacent vertebral body endplates (not shown), the implant 100 enables the adjacent vertebral bones to move relative to one another in accordance with proper anatomical motion, as further described below.

Preferably, at least one (and more preferably both) of the elements 200, 300 has at least one long-term fixation structure (e.g., flange 206, 306) having at least one feature (e.g., through hole 208a, 208b, 308) for securing the element to an adjacent vertebral body. For example, the upper element 200 has an anterior flange 206 that extends upwardly and has two through holes 208a, 208b, each of which accepts a bone screw (not shown). And, for example, the lower element 300 has an anterior flange 306 that extends downwardly and has one through hole 308 that accepts a bone screw (not shown). Once the elements 200, 300 are disposed in the intervertebral space with the vertebral body contact surfaces 202, 302 engaged with respective adjacent vertebral body endplates (not shown), securing of bone screws through the holes 208a, 208b, 308 and into the anterior surfaces of the adjacent vertebral bones helps prevent the elements from becoming dislodged from, or displaced in, the intervertebral space. Preferably, the bore axes of the through holes 208a, 208b, 308 are angled toward the adjacent vertebral body as shown.

Further preferably, at least one (and more preferably both) of the elements 200, 300 has at least one short-term fixation structure (e.g., spike 210a, 210b, 310a, 310b) for securing the element to an adjacent vertebral body (and more preferably to an adjacent vertebral body endplate). For example, each of the elements 200, 300 has a respective pair of outwardly directed spikes 210a, 210b, 310a, 310b. Once the elements 200, 300 are disposed in the intervertebral space with the vertebral body contact surfaces 202, 302 engaged with respective adjacent vertebral body endplates (not shown), the spikes 210a, 210b, 310a, 310b dig into the adjacent vertebral body endplates under the compression along the longitudinal axis of the spinal column, and thus help prevent the elements from becoming dislodged from, or displaced in, the intervertebral space. Preferably, each of the spikes 210a, 210b, 310a, 310b is sloped toward the vertebral body contact surface 202, 302 and toward the posterior direction on its posterior side as shown, to facilitate ease of insertion of the implant 100 into the intervertebral space, and is either perpendicular to the vertebral body contact surface 202, 302 on its anterior side (as shown) or sloped toward the vertebral body contact surface 202, 302 and toward the posterior direction on its anterior side (not shown), to help prevent the elements 200, 300 from anteriorly (or otherwise) slipping out of the intervertebral space.

More particularly, and referring now to FIGS. 6-12, the upper element 200 of the artificial disc implant 100 shown in FIGS. 1-5 is shown in perspective, bottom (looking longitudinally up), lateral, anterior, lateral cutaway, top (looking longitudinally down), and posterior cutaway views, respectively. Further particularly, and referring now to FIGS. 13-19, the lower element 300 of the artificial disc implant 100 shown in FIGS. 1-5 is shown in perspective, top (looking longitudinally down), lateral, anterior, lateral cutaway, bottom (looking longitudinally up), and posterior cutaway views, respectively.

As introduced above, each of the elements 200, 300 has a longitudinally outwardly directed vertebral body contact surface 202, 302. Preferably, each surface 202, 302 is shaped to conform to an endplate of an adjacent vertebral body (not shown) against which it is to be positioned. For example, inasmuch as a review of the relevant anatomy indicates that lower endplates of vertebral bones in the cervical spine each have a central concavity, it is preferable that the surface 202 is curvate (and more preferably, domed as shown, or semi-cylindrical), to conform to the central concavity. And, for example, inasmuch as a review of the relevant anatomy indicates that upper endplates of vertebral bones in the cervical spine are generally flat, it is preferable that the surface 302 is flat, as shown. It should be understood that the surfaces 202, 302 can be formed or can be dynamically formable to have these or other shapes that closely conform to the adjacent vertebral body endplate, without departing from the scope of the present invention.

Each vertebral body contact surface 202, 302 further preferably has an osteoinductive or osteoconductive feature. For example, each surface 202, 302 is preferably porous and/or roughened. This can be accomplished by any manner known in the art, including, for example, grit blasting, porous coating, etching, burning, electrical discharge machining, and sintered beading. While both surfaces 202, 302 are preferably provided with such a feature, it should be understood that only one could have such a feature without departing from the scope of the present invention. Further, it should be understood that it is not necessary for the entire surface to be so featured, but rather only a portion, some portions, or all of the surface can be so featured, or have a variety of such features, without departing from the scope of the present invention.

Each vertebral body contact surface 202, 302 further preferably has the long-term fixation and short-term fixation structures described above and denoted by corresponding reference numbers on these FIGS. 6-19.

As introduced above, the upper element 200 has a longitudinally inwardly directed articulation surface 204. Preferably, as shown, the articulation surface 204 includes a saddle surface that is defined by a concave arc (denoted by reference numeral 212 on FIG. 10) that is swept perpendicular to and along a convex arc (denoted by reference numeral 214 on FIG. 12). As best seen in FIGS. 4, 5, 10, and 12, the articulation surface 204 has a cross-section in one plane that forms a concave arc 212, and a cross-section in another plane (perpendicular to that plane) that forms a convex arc 214. The concave arc 212 has a respective substantially constant radius of curvature about an axis perpendicular to the one plane. The convex arc 214 has a respective substantially constant radius of curvature about an axis perpendicular to the other plane. Therefore, the articulation surface 204 forms a substantially constant radii saddle-shaped articulation surface.

In this preferred embodiment, as indicated in FIG. 10, the concave arc 212 has a substantially constant radius of curvature A about an axis perpendicular to the anterior-posterior plane. And, in this preferred embodiment, as indicated in FIG. 12, the convex arc 214 has a substantially constant radius of curvature B about an axis perpendicular to the lateral plane. Preferably, radius A is less than radius B, and most preferably, radius A is 0.329 and radius B is 0.340. It should be noted, however, that the present invention is not limited to any particular dimension set, and further than in some embodiments of the present invention, radius A is equal to or greater than radius B.

Also as introduced above, the lower element 300 has a longitudinally inwardly directed articulation surface 304. Preferably, as shown, the articulation surface 304 includes a saddle surface that is defined by a convex arc (denoted by reference numeral 312 on FIG. 17) that is swept perpendicular to and along a concave arc (denoted by reference numeral 314 on FIG. 19). As best seen in FIGS. 4, 5, 17, and 19, the articulation surface 304 has a cross-section in one plane that forms a convex arc 312, and a cross-section in another plane (perpendicular to that plane) that forms a concave arc 314. The convex arc 312 has a respective substantially constant radius of curvature about an axis perpendicular to the one plane. The concave arc 314 has a respective substantially constant radius of curvature about an axis perpendicular to the other plane. Therefore, the articulation surface 304 also forms a substantially constant radii saddle-shaped articulation surface.

In this preferred embodiment, as indicated in FIG. 17, the convex arc 312 has a substantially constant radius of curvature C about an axis perpendicular to the anterior-posterior plane. And, in this preferred embodiment, as indicated in FIG. 19, the concave arc 314 has a substantially constant radius of curvature D about an axis perpendicular to the lateral plane. Preferably, radius C is less than radius D, and most preferably, radius C is 0.280 inches and radius D is 0.401 inches. It should be noted, however, that the present invention is not limited to any particular dimension set, and further than in some embodiments of the present invention, radius C is equal to or greater than radius D. Further in some embodiments, radii A, B, C, and D are of equal dimension.

Importantly, the substantially constant radii saddle shaped articulation surfaces 204, 304 are configured and sized to be nestable against one another and articulatable against one another, to enable adjacent vertebral bones (against which the upper and lower elements 200, 300 are respectively disposed in the intervertebral space) to articulate in flexion, extension, and lateral bending. More particularly, as best shown in FIGS. 1-5, the artificial disc implant 100 of the present invention is assembled by disposing the upper 200 and lower 300 elements such that the vertebral body contact surfaces 202, 302 are directed away from one another, and the articulation surfaces 204, 304 are nested against one another such that the concave arc 212 accommodates the convex arc 312 and such that the convex arc 214 is accommodated by the concave arc 314. Either during or after such assembly of the implant 100, the vertebral body contact surface 202 of the upper element 200 is fixed against a lower endplate of a superior vertebral body (not shown), and the vertebral body contact surface 302 of the lower element 300 is fixed against an upper endplate of an inferior vertebral body (not shown). As noted above, the preferable long-term and short-term fixation structures on the elements 200, 300 are useful for securing the elements 200, 300 to these adjacent vertebral bones.

Accordingly, movement of the adjacent vertebral bones relative to one another is permitted by the movement of the upper 200 and lower 300 elements relative to one another. With regard to the articulation surfaces 204, 304 being configured and sized to enable the adjacent vertebral bones to articulate in flexion, extension, and lateral bending, it is understood from the described geometry and positioning of the upper 200 and lower 300 elements once the implant 100 is assembled and implanted that in flexion and extension, the concave arcs (e.g., 212) of the upper element 200 ride on the convex arcs (e.g., 312) of the lower element 300 about a center of rotation (referenced as R3 on FIG. 18) at the center of the circle defined by the convex arc 312. This center of rotation R3 is below the articulation surface 304. It is further understood from the described geometry and positioning of the upper 200 and lower 300 elements that in lateral bending, the concave arcs (e.g., 314) of the lower element 300 ride on the convex arcs (e.g., 214) of the upper element 200 about a center of rotation (referenced as R2 on FIG. 12) at the center of the circle defined by the convex arc 214. This center of rotation R2 is above the articulation surface 204. During these articulations, the elements 200, 300 are maintained at substantially constant relative distraction positions, i.e., the elements 200, 300 do not significantly move (if at all) in directions that are directed away from one another (for example, do not move in opposing axial directions from one another (e.g., along the longitudinal axis of the spine)). Accordingly, the present invention provides a pair of articulation surfaces 204, 304 that have a center of rotation above the surfaces in one mode of motion (lateral bending), and below the surfaces in another (flexion/extension), consistent in these regards with a natural intervertebral joint in the cervical spine. Preferably, the articulation surfaces 204, 304 are sized and configured so that the respective ranges of angles through which flexion/extension and lateral bending can be experienced are equal to or greater than the respective normal physiologic ranges for such movements in the cervical spine. While the present invention is not limited to any particular dimensions, a preferred embodiment has the following radii of curvature for the convex arc 312 and the convex arc 214: C=0.280 inches and B=0.340 inches. Such preferable radii of curvature provide the preferred embodiment with a flexion/extension range of plus or minus 7.5 degrees (total of 15 degrees), and a lateral bending range of plus or minus 7.5 degrees (total of 15 degrees).

While the preferred embodiment is shown with concave arc 212 having a larger constant radius of curvature A than the constant radius of curvature C of convex arc 312 (for reasons that are described in detail below), and with concave arc 314 having a larger constant radius of curvature D than the constant radius of curvature B of convex arc 214 (for reasons that are described in detail below), it should be understood that the above described functionality can also be achieved using other relative radii sizes. For example, flexion, extension, and lateral bending are also possible if the constant radius of curvature A of concave arc 212 is otherwise non-congruent with (e.g., less than) or is congruent with (i.e., equal to) the constant radius of curvature C of convex arc 312, and/or if the constant radius of curvature D of concave arc 314 is otherwise non-congruent with (e.g., less than) or is congruent with (i.e., equal to) the constant radius of curvature B of convex arc 214.

As noted above, it is preferable that, in addition to the flexion, extension, and lateral bending motions described above, the adjacent vertebral bones be permitted by the artificial disc implant 100 to axially rotate relative to one another (e.g., about the longitudinal axis of the spinal column), through a range of angles without moving in opposite (or otherwise directed away from one another) directions (e.g., along the longitudinal axis) within that range. Preferably, the articulation surfaces 204, 304 are accordingly configured and sized to permit such movement. Referring again to FIGS. 1-5, a preferred configuration is shown as an example, where the constant radius of curvature A of concave arc 212 is larger than the constant radius of curvature C of convex arc 312, and the constant radius of curvature D of concave arc 314 is larger than the constant radius of curvature B of convex arc 214. It is understood from the described geometry and positioning of the upper 200 and lower 300 elements that, because of the space, afforded by the differing radii, at the edges of the articulation surfaces 204, 304, the upper 200 and lower 300 elements are able to axially rotate relative to one another (e.g., about the longitudinal axis) through a range of angles without causing the vertebral body contact surfaces 202, 302 to move in opposite (or otherwise directed away from one another) directions (e.g., along the longitudinal axis). Once the axial rotation exceeds that range, the articulation surfaces 204, 304 interfere with one another as the concave arcs 212, 314 move toward positions in which they would be parallel to one another, and the distance between the vertebral body contact surfaces 202, 302 increases with continued axial rotation as the concave arcs 212, 314 ride up against their oppositely directed slopes. Thus, the articulation surfaces 204, 304 are configurable according to the present invention to permit normal physiologic axial rotational motion of the adjacent vertebral bones about the longitudinal axis of the spinal column through a range of angles without abnormal immediate axially opposite (or otherwise directed away from one another) movement, and to permit such axially opposite (or otherwise directed away from one another) movement when under normal physiologic conditions it should occur, that is, outside that range of angles. While the present invention is not limited to any particular dimensions, a preferred embodiment has the following radii of curvature: A=0.329 inches, B=0.340 inches, C=0.280 inches, and D=0.401 inches. Such preferable radii of curvate provide the preferred embodiment with a longitudinal axial rotation range of plus or minus 3 degrees (total of 6 degrees) before oppositely directed movement of the articulating surfaces occurs.

It should be noted that in the preferred embodiment, and in other preferable embodiments where the constant radius of curvature A of concave arc 212 is larger than the constant radius of curvature C of convex arc 312, and the constant radius of curvature D of concave arc 314 is larger than the constant radius of curvature B of convex arc 214, the articulation surfaces 204, 304 maintain point-to-point contact over a range of normal physiologic articulating movement between the adjacent vertebral bones. This is illustrated in FIGS. 4, 5, 20, and 21. More particularly, it is understood from the described geometry and positioning of the upper 200 and lower 300 elements that through flexion, extension, lateral bending, and axial rotation, the articulation surfaces 204, 304 are in point-to-point contact with one another as they are in FIGS. 4 and 5. FIGS. 20 and 21 are provided to show the implant 100 in extension and lateral bending, respectively, to further illustrate this preferable feature.

It should further be noted that in addition to the radii of curvature dimensions of the articulation surfaces 204, 304 being relevant to a configuration and sizing of the articulation surfaces 204, 304 permitting normal physiologic flexion, extension, lateral bending, and axial rotation movements of the adjacent vertebral bones, the surface area dimensions are also relevant, particularly in relation to the selected radii of curvature. More particularly, in order to provide a range of relative angulation that is within the normal physiologic range of the cervical spine, not only must the selected radii of curvature be suitable as described above, but also and accordingly the surface area of the saddle surfaces should be of a dimension that, given the selected radii of curvature, prevents the edges of the saddle surfaces (particularly the edges of the concave arcs (e.g., 212 and e.g., 314)) from hitting any surrounding anatomic structures, or other portions of the opposing element (200 or 300), before the limit of the normal physiologic range of the attempted articulation is reached. As shown, one or both of the inwardly facing surfaces of the upper 200 and lower 300 elements can be tapered inwardly before presenting its articulation surface (204 or 304), to ensure a suitable surface area dimension to prevent such interference. While the present invention is not limited to any particular surface area dimensions, the illustrated preferred embodiment has a surface area of articulation surface 204 equal to 0.146 square inches, and a surface area of articulation surface 304 equal to 0.153 square inches.

Further preferably, the articulation surfaces 204, 304 are formed of cobalt-chrome that is polished to provide a smooth bearing surface. It should be understood that the articulation surfaces 204, 304, while preferably formed of cobalt-chrome, can be additionally or alternatively formed of other metals, such as, for example, stainless steel and/or titanium, or of non-metals, such as, for example, polyethylene and/or ceramic materials (e.g., alumina and zirconia), or of any other suitable material without departing from the scope of the present invention.

It should be noted that while the present invention is illustrated and described as an artificial disc implant for use in the cervical spine, the artificial disc implant of the present invention can be adapted for use in any other portion of the spine without departing from the scope of the present invention.

While the particular prostheses for the cervical intervertebral joint of the spine as herein shown and disclosed in detail are each fully capable of obtaining the objects and providing the advantages previously stated, it shall be understood that these variations are merely illustrative of the presently preferred embodiments of the invention and that no limitations to the scope of the present invention are intended to be inferred from the details of the construction or design herein shown.

The invention claimed is:

1. A method of implanting an artificial intervertebral disc replacement comprising:
   removing a portion of an intervertebral disc from between first and second adjacent vertebrae of a spinal column; and
   implanting first and second members of an intervertebral disc replacement between the first and second vertebrae, wherein the first member includes an articular surface that defines a concave arc in sagittal plane and convex arc in a coronal plane, and the second member includes an articular surface that defines a convex arc in the sagittal plane and concave arc in the coronal plane, wherein the concave arc of the first member has a constant radius of curvature larger than a constant radius of curvature of the convex arc of the second member, and the concave arc of the second member has a constant radius of curvature larger than a constant radius of curvature of the convex arc of the first member, the radii of curvature of the concave and convex arcs of the first and second members being configured to permit the first or second members to rotate relative to each another about a longitudinal axis extending through the first and second vertebrae from a first relative position to a second relative position without movement of the first and second members axially along the longitudinal axis and from the second relative position to a third relative position in which the articular surfaces interfere with each other to cause axial separation of the first and second members along the longitudinal axis.

2. The method of claim 1, wherein the first position is an initially implanted position and the second position is a three degrees rotation of the first member relative to the second member, the second member relative to the first member, or the first and second members relative to each other about the longitudinal axis.

3. The method of claim 1, wherein the concave arc of the first member defines a first center of rotation positioned below the second member, and the concave arc of the second member defines a second center of rotation positioned above the second member.

4. The method of claim 3, wherein the second center of rotation is for lateral bending of the first and second members, while the first center of rotation is for flexion and extension of the first and second members.

5. The method of claim 1, wherein the implanting step includes inserting the first and second members between the first and second vertebrae until flanges extending from the first and second members about their respective vertebra, the flanges of the first and second members having an opening extending therethrough for receipt of a bone screw.

* * * * *